US 6,648,473 B2

(12) United States Patent
DellaVecchia et al.

(10) Patent No.: US 6,648,473 B2
(45) Date of Patent: **\*Nov. 18, 2003**

(54) HIGH-RESOLUTION RETINA IMAGING AND EYE ABERRATION DIAGNOSTICS USING STOCHASTIC PARALLEL PERTURBATION GRADIENT DESCENT OPTIMIZATION ADAPTIVE OPTICS

(75) Inventors: Michael A. DellaVecchia, Berwyn, PA (US); Larry Donoso, Philadelphia, PA (US); Mikhail A. Vorontsov, Laurel, MD (US); Gary Cathcart, Elkton, MD (US); Leonid I. Beresnev, Columbia, MD (US); Matt Banta, Baltimore, MD (US)

(73) Assignee: Philadelphia Retina Endowment Fund, Philadelphia, PA (US)

( * ) Notice: Subject to any disclaimer, the term of this patent is extended or adjusted under 35 U.S.C. 154(b) by 112 days.

This patent is subject to a terminal disclaimer.

(21) Appl. No.: 10/011,187

(22) Filed: Nov. 13, 2001

(65) Prior Publication Data

US 2003/0090628 A1 May 15, 2003

(51) Int. Cl.$^7$ .................................................. A61B 3/10
(52) U.S. Cl. ......................................................... 351/221
(58) Field of Search ................................... 351/205, 206, 351/210, 211, 212, 221, 246; 353/38, 122

(56) References Cited

U.S. PATENT DOCUMENTS

| 4,619,508 A | * 10/1986 | Shibuya et al. ............. 353/122 |
| 5,777,719 A | 7/1998 | Williams et al. |
| 5,912,731 A | 6/1999 | DeLong et al. |
| 5,949,521 A | 9/1999 | Williams et al. |
| 6,007,204 A | 12/1999 | Fahrenkrug et al. |
| 6,019,472 A | 2/2000 | Koester et al. |
| 6,086,204 A | 7/2000 | Magnante |
| 6,095,651 A | 8/2000 | Williams et al. |
| 6,143,011 A | 11/2000 | Hood et al. |
| 6,155,684 A | 12/2000 | Bille et al. |

\* cited by examiner

Primary Examiner—George Manuel
(74) Attorney, Agent, or Firm—Caesar, Rivise, Bernstein, Cohen & Pokotilow, Ltd.

(57) ABSTRACT

A method for compensating an optic aberration of an eye comprising the steps of applying to the eye a measuring light beam formed of incoherent light to provide an applied incoherent measuring light beam. An image quality metric is determined in accordance with the applied incoherent measuring light beam and the aberration is compensated in accordance with said image quality metric. A perturbation is applied to the image quality metric to provide a perturbed image quality metric and a determination is made whether a predetermined image quality is obtained in accordance with the perturbed image quality metric. An incoherent source light is transmitted from an incoherent light source to a mirror and redirected from the incoherent light source to the retina of the eye using the mirror in order to provide the applied incoherent measuring light beam.

23 Claims, 3 Drawing Sheets

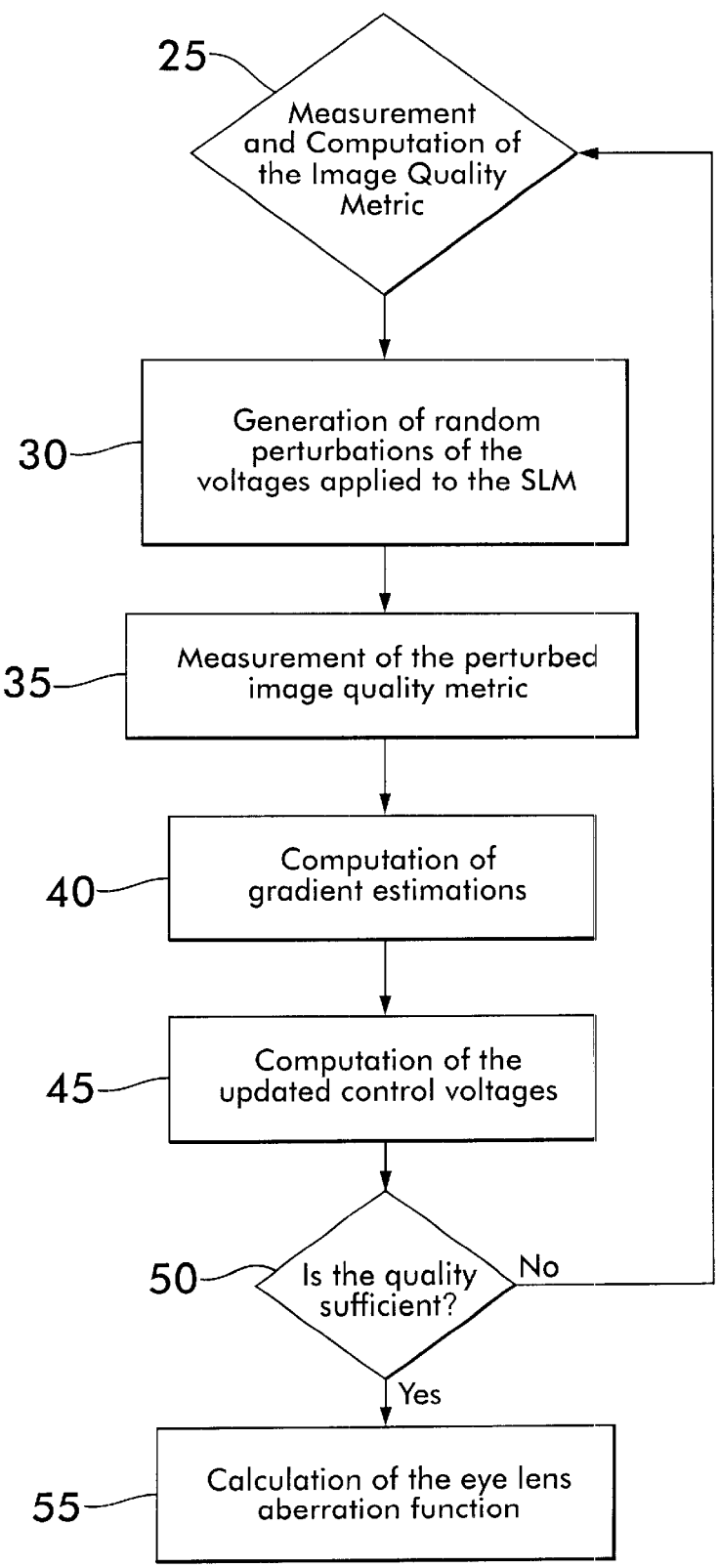

HIGH-RESOLUTION RETINA IMAGING AND EYE ABERRATION DIAGNOSTICS USING STOCHASTIC PARALLEL PERTURBATION GRADIENT DESCENT OPTIMIZATION ADAPTIVE OPTICS

FIELD OF THE INVENTION

The invention relates to a method and a system for high-resolution retinal imaging, eye aberration compensation, and diagnostics based on adaptive optics with direct optimization of an image quality metric using a stochastic parallel perturbative gradient descent technique.

BACKGROUND OF INVENTION

Adaptive optics is a promising technique for both diagnostics of optical aberrations of the eye and substantially aberration-free high-resolution imaging of the retina. In existing adaptive optics techniques adaptive correction is based on illumination of the retina by a collimated laser beam to create a small size laser spot on the retina surface with consequent measurement of phase aberrations of the wave scattered by the retina tissue. Correction of eye optical aberrations is then performed using the conventional phase conjugation technique.

This traditional approach has several important drawbacks. One important drawback is the danger due to an invasive use of the laser beam focused onto the retina. Other drawbacks include overall system complexity and the high cost of the necessary adaptive optics elements such as a wavefront sensor and wavefront reconstruction hardware. More importantly, due to aberrations the laser beam spot size on the retina is not small enough to use it as a reference point-type light source and hence conjugation of the measured wavefront does not result in optimal optical aberration correction. Additionally, the traditional approach can produce a turbid image that can make performing an operation with a microscope difficult.

One prior art method using a laser is taught in U.S. Pat. No. 6,095,651 entitled "Method and Apparatus for Improving Vision and the Resolution of Retinal Images", issued to Williams, et al. on Aug. 1, 2000. In Williams, et al. teaches a method and apparatus for improving resolution of retinal images. In this method, a point source of light is produced on the retina by a laser beam. The source is reflected from the retina and received at a lenslet array of a Hartman-Shack wavefront sensor. Thus, higher order aberrations of the eye can be measured and data can be obtained for compensating the aberrations using a system including a laser. U.S. Pat. Nos. 5,777,719 and 5,949,521 provide essentially the same teachings. While these references teach satisfactory methods for compensating aberrations, there is some small risk of damaging the retina since these methods require applying laser beams to the retina.

U.S. Pat. No. 5,912,731, entitled "Hartmann-type Optical Wavefront Sensor" issued to DeLong, et al. on Jun. 5, 1999 teaches an adaptive optics system using adjustable optical elements to compensate for aberrations in an optical beam. The aberrations may be caused, for example, by propagation of the beam through the atmosphere. The aberrated beam can be reflected from a deformable mirror having many small elements, each having an associated separate actuator.

Part of the reflected beam taught by DeLong can be split off and directed to impinge on a sensor array which provides measurements indicative of the wavefront distortion in the reflected beam. The wavefront distortion measurements can then be fed back to the deformable mirror to provide continuous corrections by appropriately moving the mirror elements. Configurations such as this, wherein the array of small lenses as referred to as a lenslet array, can be referred to as Shack-Hartmann wavefront sensors.

Additionally, DeLong teaches a wavefront sensor for use in measuring local phase tilt in two dimensions over an optical beam cross section, using only one lenslet arrangement and one camera sensor array. The measurements of DeLong are made with respect to first and second orthogonal sets of grid lines intersecting at points of interest corresponding to positions of optical device actuators. While this method does teach the way to correct aberrations in a non-laser light system, it cannot be used in the case of >>>>>>>> where lasers are required.

U.S. Pat. No. 6,007,204 issued to Fahrenkrug, et al. entitled "Compact Ocular Measuring System", issued on Dec. 28, 1999, teaches a method for determining refractive aberrations of the eye. In the system taught by Fahrenkrug, et al. a beam of light is focused at the back of the eye of the patient so that a return light path from the eye impinges upon a sensor having a light detecting surface. A microoptics array is disposed between the sensor and the eye along the light path. The lenslets of the microoptics array focus incremental portions of the outgoing wavefront onto the light detecting surface so that the deviations and the positions of the focused portions can be measured. A pair of conjugate lenses having differing focal lengths is also disposed along the light path between the eye and the microoptics array.

U.S. Pat. No. 6,019,472, issued to Koester, et al. entitled "Contact Lens Element For Examination or Treatment of Ocular Tissues" issued on Feb. 1, 2000 teaches a multi-layered contact lens element including a plurality of lens elements wherein a first lens element has a recess capable of holding a volume of liquid against a cornea of the eye. A microscope is connected to the contact lens element to assist in the examination or treatment of ocular tissues.

U.S. Pat. No. 6,086,204, issued to Magnante entitled "Methods and Devices To Design and Fabricate Surfaces on Contact Lenses and On Corneal Tissue That Correct the Eyes Optical Aberrations" on Jul. 11, 2000. Magnante teaches a method for measuring the optical aberrations of an eye either with or without a contact lens in place on the cornea. A mathematical analysis is performed on the optical aberrations of the eye to design a modified shape for the original contact lens or cornea that will correct the optical aberrations. An aberration correcting surface is fabricated on the contact lense by a process that includes laser ablation and thermal molding. The source of light can be coherent or incoherent.

U.S. Pat. No. 6,143,011, issued to Hood, et al. entitled "Hydrokeratome For Refractive Surgery" issued on Nov. 7, 2000 teaches a high speed liquid jet for forming an ophthalmic incisions. The Hood, et al. system is adapted for high precision positioning of the jet carrier. An airway beam may be provided by a collimated LED or laser diode. The laser beam can be used to align the system.

U.S. Pat. No. 6,155,684, issued to Billie, et al. entitled "Method and Apparatus for Precompensating The Refractive Properties of the Human Eye With Adaptive Optical Feedback Control" issued on Dec. 5, 2000. Billie, et al. teaches a system for directing a beam of light through the eye and reflecting the light from the retina. A lenslet array is used to obtain a digitized acuity map from the reflected light for generating a signal that programs an active mirror. In accordance with the signal the optical paths of individuals beams in and the beam of light are made to appear to be substantially equal to each other. Thus, the incoming beam can be precompensated to allow for the refractive aberrations of the eyes that are evidenced by the acuity map.

Additional methods for using adaptive optics to compensate for aberrations of the human eye are taught in J. Liang, D. Williams and D. Miller, "Supernormal Vision and High-Resolution Retinal Imaging Through Adaptive Optics," J. Opt. Soc. Am. A, Vol. 14, No. 11, pp. 2884–2891,1997 and F. Vargas-Martin, P. Prieto, and P. Artal, "Correction of the Aberrations in the Human Eye with a Liquid-Crystal Spatial Light Modulator: Limits to Performance," J. Opt. Soc. Am. A, Vol. 15, No. 9, pp. 2552–2561, 1998. Additionally, J. Liang, B. Grimm, S. Goelz, and J. Bille, "Objective Measurement of Wave Aberrations of the Human Eye with the Use of a Hartmann-Shack Wave-Front Sensor," J. Opt. Soc. Am. A, Vol. 11, No. 7, pp. 1949–1957,1994 teaches such a use of adaptive optics.

Furthermore, it is known in the art to use a PSPGD optimization algorithm in different applications. For example, see M. Vorontsov, and V. Sivokon, "Stochastic Parallel-Gradient-Descent Technique for High-Resolution Wave-Front Phase-Distortion Correction," J. Opt. Soc. Am. A, Vol. 15, No. 10, pp. 2745–2758,1998. Also see M. Vorontsov, G. Carhart, and J. Ricklin, "Adaptive Phase-Distortion Correction Based on Parallel Gradient-Descent Optimization," Optics Letters, Vol. 22, No. 12, pp. 907–909, 1997.

SUMMARY

The present inventions deal with new methods of high-resolution imaging of the retina, and adaptive correction and diagnostics of eye optical aberrations using adaptive optics techniques based on parallel stochastic perturbative gradient descent (PSPGD) optimization. This method of optimization is also known as simultaneous perturbation stochastic approximation (SPSA) optimization. Compensation of optical aberrations of the eye and improvement of retina image resolution can be accomplished using an electronically controlled phase spatial light modulator (SLM) as a wavefront aberration correction interfaced with an imaging sensor and a feedback controller that implements the PSPGD control algorithm.

Examples of the electronically-controlled phase SLMs include a pixelized liquid-crystal device, micro mechanical mirrorarray, and deformable, piston or tip-tilt mirrors. Wave-front sensing can be performed at the SLM and the wavefront aberration compensation is performed using retina image data obtained with an imaging camera (CCD, CMOS etc.) or with a specially design very large scale integration (VLSI) imaging chip (VLSI imager). The retina imaging data are processed to obtain a signal characterizing the quality of the retinal image (image quality metric) used to control the wavefront correction and compensate the eye aberrations.

The image quality computation can be performed externally using an imaging sensor connected with a computer or internally directly on an imaging chip. The image quality metric signal is used as an input signal for the feedback controller. The controller computes control voltages applied to the wavefront aberration correction. The controller can be implemented as a computer module, a field programmable gate array (FPGA) or a VLSI micro-electronic system performing computations required for optimization of image quality metrics based on the PSPGD algorithm.

The use of the PSPGD optimization technique for adaptive compensation of eye aberration provides considerable performance improvement if compared with the existing techniques for retina imaging and eye aberration compensation and diagnostics. The first advantage is that the PSPGD algorithm does not require the use of laser illumination of the retina and consequently significantly reduces the risk of retina damage caused by a focused coherent laser beam. A further advantage is that the PSPGD algorithm does not require the use of a wavefront sensor or wavefront aberration reconstruction computation. This makes the entire system low-cost and compact if compared with the existing adaptive optics systems for retina imaging. Additionally, the PSPGD algorithm can be implemented using a parallel analog, mix-mode analog-digital or parallel digital controller because of its parallel nature. This significantly speeds up the operations of the PSPGD algorithm, providing continuous retina image improvement, eye aberration compensation and diagnostics.

Thus, in the adaptive correction technique of the present invention neither laser illumination nor wavefront sensing are required. Optical aberration correction is based on direct optimization of the quality of a retina image obtained using a white light, incoherent, partially coherent imaging system. The novel imaging system includes a multi-electrode phase spatial light modulator, or an adaptive mirror controlled with a computer or with a specially designed FPGA or VLSI system. The calculated image quality metric is optimized using a parallel stochastic gradient descent algorithm. The adaptive optical system is used in order to compensate severe aberrations of the eye and thus provide a high-resolution image of the retina tissue and the eye aberration diagnostic.

DESCRIPTION OF THE DRAWINGS

FIG. 2 shows a flow chart representation of control algorithm suitable for use in the system of FIG. 1 when practicing the method of the present invention.

DETAILED DESCRIPTION OF THE PREFERRED EMBODIMENTS

Figure 1A:
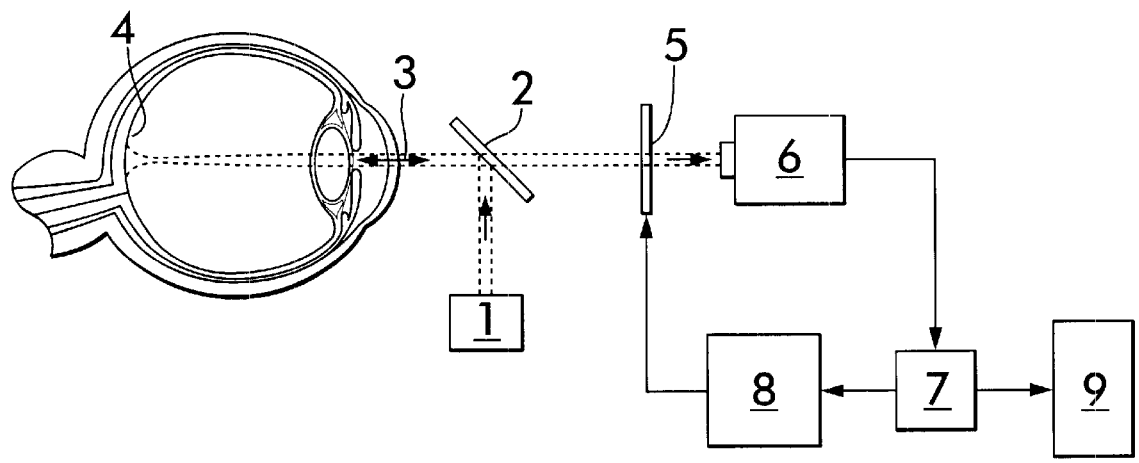
FIGS. 1A,B show a schematic representation of system suitable for practicing the eye aberration correcting method of the present invention.
Figure 1B:
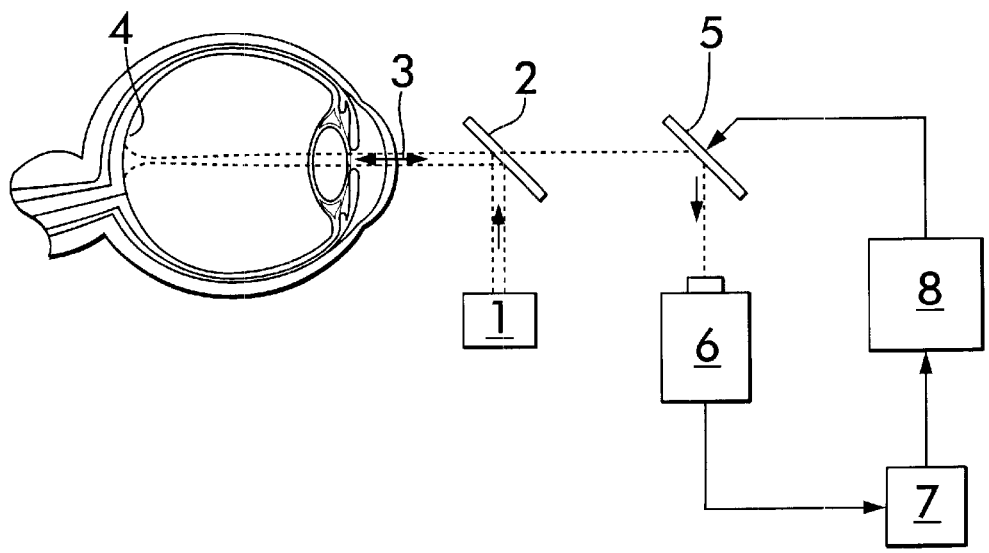

Referring now to FIG. 1, there is shown a schematic representation of the aberration correcting system 10 of the present invention. In the aberration correcting system 10 a light beam from a white light source 1 is redirected by a mirror 2 in order to cause it to enter an eye. In accordance with the present invention the white light beam from the light source 1 can be any kind of incoherent light.

The light from the mirror 2 reaches the retina 4 of the eye and reflected light exits the eye to provide two light beams, one passing in each direction, as indicated by arrow 3. The exiting light beam then passes through an SLM 5. The light beam from the SLM 5 enters an image sensor 6. The image sensor 6 can be a charge coupled capacitor device or any other device capable of sensing and digitizing the light beam from the SLM 5.

The imaging sensor 6 can include an imaging chip for performing the calculations required to determine an image quality metric. The image quality metric can thus be computed on the imaging chip directly or it can be calculated using a separate computational device/computer 7 that calculates the image quality metric of the retina image. It is the use of a digitized image in this manner that permits the use of an incoherent light rather than a coherent light within the aberration correction correcting system 10.

The computational device 7 sends a measurement signal representative of the image quality metric to a controller 8. The controller 8 implements a PSPGD algorithm by computing control voltages and applying the computed control voltages to the SLM 5. The PSPGD algorithm used by the controller 8 can be any conventional PSPGD algorithm known to those of ordinary skill in the art. In the preferred embodiment of the invention, the controller 8 continuously receives digital information about the quality of the image and continuously updates the control voltages applied to the SLM 5 until the quality of the retina image is optimized.

Figure 3A:
FIGS. 3A,B show images of an artificial retina before and after correction of an aberration.

Referring now to FIGS. 2 and 3A, B there are shown a flow chart representation of a portion of a PSPGD control algorithm 20 for use in cooperation with the aberration correcting system 10 in order to practice the present invention as well as representations of the corrected image, both before and after correction. In order to simplify the drawing a single iterative step of the PSPGD control algorithm 20 is shown with a loop for repeating the single iterative step until the quality of the compensation is acceptable.

In step 25 of the PSPGD control algorithm 20 a measurement and calculation of the image quality metric is performed. This step includes the retinal image capture and the calculation of the image quality metric performed by the sensor 5 and the computational device 7 in the aberration correcting system 10. The image captured at the beginning of the operation of the PSPGD control algorithm 20 can be substantially as shown in FIG. 3A.

One can use any relevant entity as an image quality metric. For example, in one embodiment of the PSPGD control algorithm 20 the image quality metric can be the sharpness function. A sharpness function suitable for use in the present invention can be defined as $$J=\int|\nabla^2 I(x,y)|dxdy$$

where I (x,y) is the intensity distribution in the image, and $\nabla^2$ is the Laplacian operator over the image. The Laplacian can be calculated by convolving the image with a Laplacian kernel. The convolving can involve a special purpose VLSI microchip. Alternately, the convolving can be performed using a computer that takes a picture of the image using a digital camera. In another embodiment different digital high-pass filters can be used rather than the Laplacian operator.

Additionally, a frequency distribution function can be used rather than a sharpness function when determining the image quality metric. The use of a frequency distribution function allows the system to distinguish tissues of different colors. This is useful where different kinds of tissue, for example, different tumors, have different colors. Locating tumors in this manner also permits the invention to provide tumor location information, such as a grid location on a grid having a pre-determined reference in order to assist in diagnosis and surgery. It also permits the invention to provide tumor size and type information. Additionally, the use of a frequency distribution function permits a surgeon to determine which light frequencies are best for performing diagnosis and surgery.

The image quality metric J can also be calculated either optically or digitally using the expression introduced in:

$$J=\int|F\{exp[i\gamma I(x,y)]\}|^4 dxdy$$

where F is the Fourier transform operator and $\gamma$ is a parameter that is dependent upon the dynamic range of the used image.

In step 30 of the PSPGD control algorithm 20 random perturbations in the voltages applied to the SLM 5 electrodes are generated. The SLM 5 can be a liquid crystal membrane for modifying the light beam according to the electrical signals from controller 8 in a manner well understood by those skilled in the art.

In order to generate the perturbations for application to the electrodes for the SLM 5 random numbers with any statistical properties can be used as perturbations. For example, uncorrelated random coin flip perturbations having identical amplitudes $|du_j|=p$ and the Bernoulli probability distribution:

$$\delta u_j=\pm\pi, Pr(\delta u_j=+\pi)=0.5$$

for all j=1, . . . , N(N=the number of control channels) and iteration numbers can be used. Note that Non-Bernoulli perturbations are also allowed in the PSPGD control algorithm 20.

In step 35 of the PSPGD control algorithm 20 a measurement of the perturbed image quality metric and a computation of the image quality perturbation $\delta J^{(m)}$ are performed. Following the determination of the perturbed image quality metric, the gradient estimations:

$$J'^{(m)}_j=\delta J^{(m)}\pi_j^{(m)}$$

are computed as shown in step 40.

The updated control voltages are then determined as shown in step 45. Therefore, a calculation of:

$$u_j^{(m+1)}=u_j^{(m)}-\gamma\delta J^{(m)}\pi_j^{(m)}, j=1, \ldots, N$$

is performed.

To further improve the accuracy of gradient estimation in the PSPGD control algorithm 20 a two-sided perturbation can be used. In a two-sided perturbation two measurements of the cost function perturbations $\delta J^+$ and $\delta J^-$ are taken. The two measurements correspond to sequentially applied differential perturbations $+\delta u_j/2$ and $-\delta u_j/2$. It follows that:

$$\delta J=\delta J^+-\delta J^-$$

and $$J'_j=\delta J\delta u_j,$$

which can produce a more accurate gradient estimate.

Figure 3B:
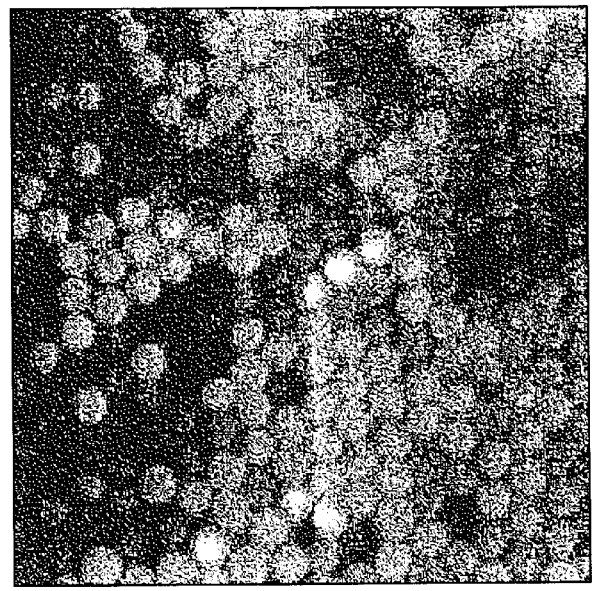

The process steps 25–45 of the PSPGD control algorithm 20 are repeated iteratively until the image quality metric has reached an acceptable level as determined in step 50. The choice of an acceptable level of the image quality metric is a conventional one well known to those skilled in the art. As shown in step 55 the aberration is then corrected and an image of the retina can be taken. The image resulting from the operation of the PSPGD algorithm 20 can be as shown in FIG. 3B.

The eye aberration function $\phi(x,y)$ can be calculated from known voltages applied to wavefront correction $\{u_j\}$ at the end of the iterative optimization process and known response functions of $\{S_j(x,y)\}$ wavefront correction $$\varphi(x, y) = \sum_{j=1}^{N} u_j S_j(x, y).$$

The description herein will so fully illustrate my invention that others may, by applying current or future knowledge, adopt the same for use under various conditions of service.

For example, the invention may be used for the determination of spectacle, contact lens, intralocular lens (phakic and aphakic), intracorneal lens or rings, or other means of refractive alterations. When making lenses using the present invention, the best data obtained using the optimization features can be transmitted from computation device 7 to a conventional lens making device 9. Lens making device 9 can be any conventional device for making lenses according to such data since the parameters optimized by the invention are the same parameters required for visual activity using the lens.

We claim:

1. A method for compensating an optic aberration of an eye, comprising the steps of:
    (a) applying to said eye a measuring light beam formed of incoherent light to provide an applied incoherent measuring light beam;
    (b) determining an image quality metric in accordance with said applied incoherent measuring light beam; and
    (c) compensating said aberration in accordance with said image quality metric.

2. The method for compensating an optic aberration of eye of claim 1, further comprising the steps of:
    (a) applying a perturbation to said image quality metric to provide a perturbed image quality metric; and
    (b) determining whether a predetermined image quality is obtained in accordance with said perturbed image quality metric.

3. The method for compensating optic aberrations of an eye of claim 1, further comprising the steps of:
    (a) transmitting incoherent source light from an incoherent light source to a mirror; and
    (b) redirecting said incoherent source light from said incoherent light source to the retina of said eye using said mirror in order to provide said applied incoherent measuring light beam.

4. The method for compensating optic aberrations of a eye of claim 1, further comprising the steps of reflecting said applied incoherent measuring light beam from said retina to provide a reflected light beam and applying said reflected light beam to a spatial light modulator.

5. The method for compensating optic aberrations of an eye of claim 4, further comprising the steps of applying said reflected light beam from said spatial light modulator to an image sensor for sensing said reflected light and providing signals representative of said reflected light.

6. The method for compensating optic aberrations of an eye of claim 5, further comprising the step of determining said image quality metric in accordance with said signals representative of said reflected light.

7. The method for compensating optic aberrations of an eye of claim 6, further comprising the step of determining said image quality metric as:

$$J=\int |F\{\exp[i\gamma I(x,y)]\}|^4 dxdy$$

where F is a Fourier transform and $\gamma$ is a parameter dependent upon a dynamic range of said reflected light beam.

8. The method for compensating optic aberrations of an eye of claim 7, further comprising the step of optimizing said control voltage using a parallel stochastic perturbative gradient descent algorithm.

9. The method for compensating optic aberrations of an eye of claim 8, further comprising the step of performing a wavefront aberration reconstruction computation.

10. The method for compensating an optic aberration of an eye of claim 9, including a wavefront sensor wherein the step of compensating said aberration comprises the step of compensating a plurality of wavefronts.

11. The method for compensating optic aberrations of an eye of claim 6, further comprising the step of computing a control voltage in accordance with said image quality metric.

12. The method for compensating an optic aberration of an eye of claim 11, further comprising the step of applying said control voltage to said spatial light modulator for modulating said reflected light in accordance with said control voltage.

13. The method for compensating an optic aberration of an eye of claim 12, further comprising the step of applying a voltage perturbation to aid control voltage in accordance with said perturbation applied to said image quality metric.

14. The method for compensating an optic aberration of an eye of claim 13, wherein said voltage perturbation comprises a random voltage perturbation.

15. The method for compensating an optic aberration of an eye of claim 14, further comprising a plurality of random voltage perturbations having identical peturbation amplitudes.

16. The method for compensating an optic aberration of an eye of claim 14, wherein said random voltage perturbation comprises a plurality of voltage perturbations having a Bernoulli probability distribution.

17. The method for compensating an optic aberration of an eye of claim 14, wherein said random voltage perturbation comprises a plurality of sequentially applied differential voltage perturbations $+du_j/2$ and $-du_j/2$.

18. The method for compensating optic aberrations of an eye of claim 4, wherein said image quality metric is a sharpness function.

19. The method for compensating an optic aberration of an eye of claim 18, wherein said sharpness function comprises:

$$J=\int |\nabla^2 I(x,y)| dxdy$$

and I(x,y) is an intensity distribution of the image quality metric and $\nabla^2$ is a Laplacian operator over said image quality metric.

20. The method for compensating an optic aberration of an eye of claim 1, further comprising the step of determining a refractive state of said eye in accordance with said compensating.

21. The method for compensating an optic aberration of an eye of claim 1, further comprising the step of altering said refractive state of said eye in accordance with said compensating.

22. The method for compensating an optic aberration of an eye of claim 1, further comprising the step of determining a disease diagnosis of said eye in accordance with said compensating.

23. The method for compensating an optic aberration of an eye of claim 1, further comprising the step of performing surgery on said eye in accordance with said compensating.

* * * * *